United States Patent [19]

Effland et al.

[11] 4,045,448
[45] Aug. 30, 1977

[54] PYRROLO[2,1-c][1,4]BENZOXAZEPINE AND BENZOXAZOCINE DERIVATIVES

[75] Inventors: Richard C. Effland, Bridgewater; Larry Davis, Flemington, both of N.J.; Wolfgang Schaub, Kelkheim, Germany

[73] Assignee: American Hoechst Corporation, Bridgewater, N.J.

[21] Appl. No.: 661,533

[22] Filed: Feb. 26, 1976

[51] Int. Cl.$^2$ ............................................. C07D 498/04
[52] U.S. Cl. .......................... 260/326.5 B; 260/313.1; 260/326.5 J; 260/326.5 R; 260/570.9; 424/274
[58] Field of Search ................................. 260/326.5 B

[56] References Cited

U.S. PATENT DOCUMENTS 3,888,946   6/1975   Pavs et al. ..................... 260/326.5 B

OTHER PUBLICATIONS

Houlihan et al., Chem. Abst., 75:49157u of (Ger. Offen. 2,050,344, Apr. 29, 1971).
Nacci et al., Chem. Abst., (1973), 78:43450z and 79:78762a.

Primary Examiner—Donald G. Daus
Assistant Examiner—David E. Wheeler
Attorney, Agent, or Firm—Curtis, Morris & Safford

[57] ABSTRACT

Novel pyrrolobenzoxazalkanes, physiologically tolerable acid addition salts thereof and a method of preparing same are described. Compounds of the present invention are useful as analgesic, tranquilizing and anticonvulsant agents.

9 Claims, No Drawings

PYRROLO[2,1-c][1,4]BENZOXAZEPINE AND BENZOXAZOCINE DERIVATIVES

This invention relates to novel pyrrolobenzoxazalkanes and to their physiologically tolerable acid addition salts which are useful as analgesics, to methods of treatment with pharmaceutically effective amounts thereof and to pharmaceutical compositions containing such compounds as essential active ingredients. Additionally compounds of the invention are further useful as tranquilizers and anticonvulsants.

To the best of our knowledge, the compounds of this invention have not heretofore been described or suggested. The compounds herein disclosed have a new tricyclic ring structure and display significant pharmacological activity as analgesics, anticonvulsants and tranquilizers.

The compounds of the present invention have the formula

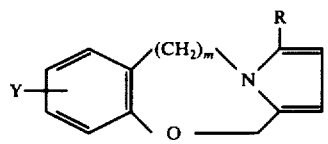

wherein Y is hydrogen, halogen, lower alkoxy, lower alkyl, trifluoromethyl, nitro or amino; R is hydrogen, halogen, CHO, CH(OH)(CH$_2$)$_n$R$^1$, an imino radical of the formula CH=NR$^2$ or a methylaminoalkyl of the formula

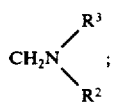

R$^1$ is hydrogen or

R$^2$ is alkyl, phenylloweralkyl, alkylaminoalkyl, dialkylaminoalkyl or diphenylloweralkyl of the formula

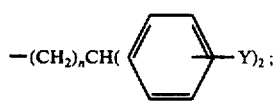

R$^3$ is hydrogen, alkyl, cycloalkylloweralkyl or phenylloweralkyl; m is the integer 1 or 2 and n is an integer from 1 to 4; and the acid addition salts thereof. In the above definitions loweralkyl and loweralkoxy mean those radicals of from 1 to 4 carbon atoms, alkyl and cycloalkyl mean radicals of up to 6 carbon atoms, halogen means chlorine, bromine, iodine and fluorine and phenyl includes substituted phenyls wherein the substituents are as recited in the definition of Y.

Preferred embodiments of the present invention are those compounds wherein m is 1, Y is hydrogen and R is a methylaminoalkyl of the formula

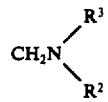

While some compounds of the invention are less active than others they are nevertheless useful as intermediate for the more active compounds. This will become readily apparent in the methods of preparation detailed below.

Acids useful for preparing the acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The compounds of the present invention are prepared by the several methods of preparation which are outlined below. In these methods m and Y are as defined earlier.

Method A

1. An orthofluorophenylalkylamine of the formula

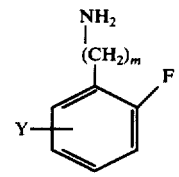

is reacted with 2,5-dimethoxytetrahydrofuran to produce an orthofluorophenylalkylpyrrole of the formula

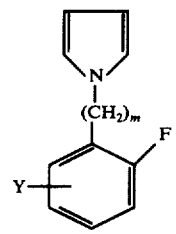

Compounds of the formula (I) wherein m is 1 can be obtained by brominating a 2-fluorotoluene to produce a 2-fluorobenzylbromide; reacting the 2-fluorobenzylbrmode with potassium phthalimide by a Gabriel's synthesis to form a corresponding N-benzyl-phthalimide and cleaving the phthalimide by thermal addition of hydrazine to form a 2-fluorobenzylamine of formula (I).

Compounds of formula (I) wherein m is 2 can be obtained by chlorinating a 2-fluorotoluene to produce a 2-fluorobenzylchloride reacting the benzyl chloride with sodium cyanide to form the corresponding benzyl cyanide and reducing the cyano radical with diborane to produce a 2-fluorophenethylamine of formula (I).

2. An aldehyde of the formula

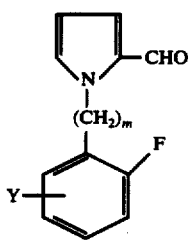

is prepared from the orthofluorophenylalkylpyrrole by a method known to the art. One such method is the Vilsmeier-Haack reaction described in Chem. Ber. 60, 119 (1927).

3. The aldehyde is reduced to a corresponding pyrrylaminomethanol by a method known to the art. A preferred method utilizes sodium borohydride in isopropyl alcohol at 80° C as the reduction medium.

4. The reaction of a pyrrylaminomethanol with a mineral base produces a tricyclic compound of the present invention of the formula

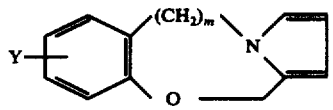

A preferred method utilizes sodium hydride as the base in the presence of an organic solvent such as dry benzene or dimethylformamide.

Method B

An aldehyde of the formula

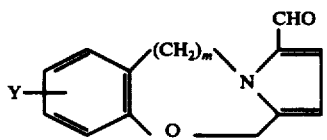

is prepared from a compound prepared in Method A, step 4 by the procedure described in Method A, step 2.

Method C

1. An imino compound of the formula

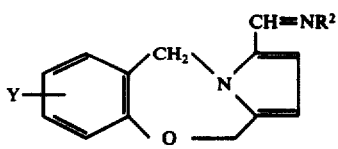

wherein $R^2$ is as defined earlier is prepared by reacting an aldehyde prepared in Method B with a primary amine under conditions of the Schiff reaction.

Method D

The reduction of an imino compound prepared in method C by the procedure of Method A, step 3 produces a secondary amine of the formula

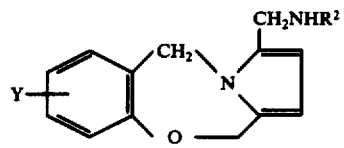

wherein $R^2$ is as defined as earlier.

Method E

The alkylation by a method known to the art of a secondary amine prepared in Method D produces a tertiary amine of the formula

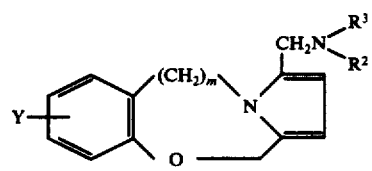

wherein $R^2$ is as defined earlier and $R^3$ is alkyl, cycloalkylloweralkyl or phenylloweralkyl. One such method of preparing such a tertiary amine comprises acylating the secondary amine with a carbonyl halide of the formula

wherein $R^4$ is lower alkyl, lower alkoxy, cycloalkyl of from 3 to 6 carbon atoms, phenyl of phenylalkyl of from 7 to 9 carbon atoms in the presence of an organic solvent and an acid scavenger to produce a N-carbonyl compound and reducing the N-carbonyl compound by a standard method such as with lithium aluminium hydride.

Method F

An alcohol of the formula

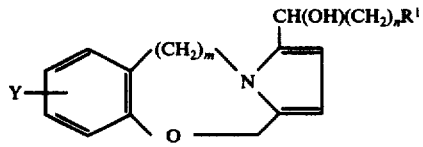

wherein $n$ and $R^1$ are as defined earlier is prepared by reacting an aldehyde prepared in Method B with a suitable Grignard reagent under standard Grignard conditions.

The compounds of the present invention are useful as analgesic agents due to their ability to alleviate pain in mammals. This analgesic activity of representative compounds of the invention is demonstrated in the phenyl-2-quinone-induced writhing assay in mice, a standard assay for analgesia [Proc. Soc. Exptl. Biol. Med., 95, 729 (1957)]. Thus for instance a 64% inhibition of writhing is effected by a 10 mg/kg subcutaneous dose of 1-[(N-phenethyl)aminomethyl]-4H,-10H-pyrolo[2,1-c][1,4]benzoxazepine-hydrochloride. The ability of 25 mg/kg subcutaneous doses of other compounds to inhibit writhing is given below in Table I

Table I

| Compound | % Inhibition of Writhing |
|---|---|
| 4-Dimethylamino-1-(4H,10H-pyrrolo[2,1-c]-[1,4]benzoxazepine-1-yl)-1-butanol | 67 |
| 1-[4,4-Bis-(4-fluorophenyl)butylaminomethyl]-4H,10H-pyrrolo[2,1-c][1,4]benzoxazepine | 67 |
| 1-[4,4-Bis-(4-fluorophenyl)butyliminomethyl]-4H,10H-pyrrolo[2,1-c][1,4]benzoxazepine-hydrochloride | 48 |
| 1-Methylaminomethyl-4H,10H-pyrrolo[2,1-c]-[1,4]benzoxazepine hydrochloride | 32 |
| 1-Methyliminomethyl-4H,10H-pyrrolo[2,1-c][1,4]benzoxazepine | 17 |

These data indicate that the compounds of the invention are useful for the alleviation of pain in mammals when administered in amounts ranging from about 0.1 to about 100 mg/kg of body weight per day.

Compounds of the present invention are further useful as tranquilizers due to their depressant action on the central nervous system (CNS) of mammals. This activity is demonstrated in the mouse observation procedure, a standard assay for CNS depressants [Psychlopharmacologia, 9, 259 (1966)]. Thus, for instance, the minimum effective dose (MED) at which 1-methylaminomethyl-4H,10H-pyrrolo-[2,1-c][1,4]benzoxazepine.hydrochloride displays significant effects on behavior and reflex depression together with muscle relaxation is 3mg/kg. Similar effects on behavior and reflex depression are exhibited by 1-[4,4-bis-(4-fluorophenyl)butylaminomethyl]-4-H,10H-pyrrolo[2,1-c][1,4]benzoxazepine, 1-(N-methyl-N-phenethylaminomethyl)-4H,10H-pyrrolo [2,1-c][1,4]benzoxazepine.hydrochloride and 1-dimethylaminomethyl-4H,10H-pyrrolo[2,1-c][1,4]benzoxazepine.hydrochloride at a MED of 30 mg/kg. These data indicate that compounds of the present invention are useful as tranquilizers in mammals when administered in amounts ranging from about 0.1 to 100 mg/kg of body weight per day.

Compounds of the present invention are still further useful as anticonvulsant agents for mammals as demonstrated in the method of Woodbury, L. A. and Davenport, V. D., in Arch. Int. Pharmacodynam, Vol. 92, (1952) at pages 97-107. For example, 50 mg/kg intraperitoneal doses of 4-dimethylamino-1-(4H,-10H-pyrrolo[2,1-c][1,4benzoxazepine-1-yl)-1-butanol and 1-dimethylaminomethyl-4H,10-pyrrolo[2,1-c][1,4]benzoxazepine.hydrochloride produce a 100% and 33% protection from the effect of supra maximal electro shock, respectively. These data indicate that compounds of the invention are useful for treating convulsion in mammals when administered in amounts ranging from about 0.1 to 100 mg/kg of body weight per day.

Further examples of compounds of the invention are:
8-Amino-4H,10H-pyrrolo[2,1-c][1,4]benzoxazepine;
7-Fluoro-4H,10H-pyrrolo[2,1c][1,4]benzoxazepine-1-carboxaldehyde;
1,(4H,10H-Pyrrolo[2,1-c][1,4]benzoxazepin-1-yl)-1-pentanol;
1-(10,11-Dihydro-4H-pyrrolo[2,1-c][1,4]benzoxazocine-1-yl)-1-ethanol;
3-Isopropylamino-1-(4H,10H,pyrrolo[2,1-c][1,4]benzozapin-1-yl)-1-propanol;
1-Propyliminomethyl-2-(4-trifluoromethylphenyl)-4H,10H-pyrrolo[2,1-c][1,4]benzoxazepine;
1-[4,4Bis-phenylbutyliminomethyl]-4H,10H-pyrrolo[2,1-c][1,4]benzoxazepine;
1-N-methyl-N-pentylaminoethyliminomethyl-7-trifluoromethyl-4H,10H-pyrrolo[2,1-c][1,4]benzoxazepine;
1-n-Hexylaminomethyl-4H,10H-pyrrolo[2,1-c][1,4]benzoxazepine;
10,11-Dihydro-1-isopropylaminomethyl-4H-pyrrolo[2,1-c]-[1,4]-benzoxazocine;
1-(N-cyclopropylmethyl-N-ethylaminomethyl)-4H,10H-pyrrolo-[2,1-c][1,4]benzoxazepine;
1-(N-benzyl-N-methylaminomethyl)-4H,10H-pyrrolo[2,1-c][1,4]-benzoxazepine;
10,11-Dihydro-1-(N,N-phenethylamino)methyl-4H-pyrrolo[2,1-c][1,4]benzoxazocine;
1-Dimethylaminomethyl-7-methyl-4H,10H-pyrrolo[2,1-c][1,4]-benzoxazepine;
10,11-Dihydro-8-nitro-4H-pyrrolo[2,1-c][1,4benzoxazocine;
4-Ethylamino-7-ethoxy-1-(4H,10H-pyrrolo[2,1-c][1,4]-benzoxazepin-1-yl)butanol; and
1-[(N-diethylaminoethyl)aminomethyl]-4H,10H-pyrrolo[2,1-c][1,4]benzoxazepine;
1-[(N-dimethylaminopentyl)aminomethyl]-4H,10H-pyrrolo[2,1-c][1,4]benzoxazepine;
1-[(N-cyclopropylmethyl-N-diisopropylaminopropyl)aminomethyl]-4H,10H-pyrrolo[2,1-c][1,4]benzoxazepine.

Effective quantities of the compounds of the invention may be administered to a patient by any one of various methods, for example, orally as in capsules or tablets, parenterally in the form of sterile solutions or suspensions, and in some cases intraveneously in the form of sterile solutions. The free base final products, while effective themselves, may be formulated and administered in the form of their phamaceutically acceptable addition salts for purposes of stability, convenience of crystallization, increased solubility and the like.

The active compounds of the present invention may be administered to patients orally, for example, with an inert diluent or with an edible carrier, or enclosed in gelatin capsules, or in the form of compressed tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but this may be varied depending upon the particular form and may conveniently be between 4 to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

Tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like, a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to active compounds, sucrose as a sweetening agent, and certain preservatives, dyes, colorings and flavors. Materials used in preparing these various compositions should be pharmaceutically pure and non-toxic in the amounts used.

For the purpose of parenteral therapeutics administration, the active compounds of the invention may be incorporated into a solution or suspension in concentrations of between 0.5 and about 30% of the weight thereof. They should contain at least 0.5L of active compound. The amount of active compound in such compositions should be such that a suitable dosage will be obtained. Preferably, compositions and preparations according to the present invention are prepared so that parenteral dosage units contain between 0.5 to 100 milligrams of active compound.

Solutions or suspensions of the active compounds may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. Parenteral preparations can be enclosed in ampules, disposable syringes or multiple dose vials made of glass or plastic.

The present invention is further illustrated by the following examples:

EXAMPLE 1 a. 8 g of dimethylformamide are cooled to 5° C in a 500 ml three neck round bottom flask and 16.9 g of phosphorus oxychloride are added dropwise with stirring while maintaining the temperature below 20° C. After total addition, the mixture is stirred at ambient temperature for 15 minutes, 25 ml of ethylene dichloride are introduced and the solution is cooled to 5° C. The temperature of the solution is maintained at this low temperature with stirring during the addition of a solution of 17.5 g of 1-(2-flurorbenzyl)pyrrole, Example 1a, in 25 ml of ethylene dichloride. The reaction solution is stirred at this temperature for 30 minutes at ambient temperature for an additional 30 minutes and then refluxed under nitrogen for 5 hours. The mixture is allowed to cool to ambient temperature and a solution of 75 g of sodium acetate trihydrate in 120 ml of water is added. The two phase mixture is stirred vigorously at ambient temperature for 15 minutes and then refluxed for 30 minutes. After the reaction mixture cools to ambient temperature the ethylene dichloride layer is removed and the aqueous phase is extracted with ether. The combined organic extracts are washed twice with a saturated sodium carbonate solution and once with a saturated sodium chloride solution and dried. Removal of the solvent leaves a light yellow oil which solidifies upon standing to a pale yellow solid which is recrystallized from an ether-hexane mixture to give nearly white crystals, mp 39°-41° C, of 1-(2-fluorobenzyl)pyrrole-2-carboxaldehyde.

b. To a stirring suspension of 4.4 g sodium borohydride in 100 ml of isopropyl alcohol is added dropwise a solution of 11.7 g of 1-(2-fluorobenzyl)pyrrolo-2-carboxaldehyde in 100 ml of isopropyl alcohol. After total addition the reaction mixture is stirred at 80° C. for 20 hours and then the isopropyl alcohol is evaporated off leaving a white semi-solid. The semi-solid is stirred with 500 ml of water and then extracted into ether. The combined ether extracts are washed with water, dried and filtered and the ether evaporated off leaving a clear oil of [1-(2-fluorobenzyl)-2-pyrryl]methanol. Infrared and nuclear magnetic resonance spectra confirm this structure.

c. To a suspension of 2.9 g of sodium hydride in 100 ml of benzene is added dropwise a solution of 11.7 g of [1-(2-fluorobenzyl)-2-pyrryl]methanol in 50 ml of benzene. After total addition the mixture is stirred at reflux for 1 hour, then 20 ml of dimethylformamide is added and stirring is continued at 80° C for 6 additional hours. The reaction mixture is cooled, poured into 1.5 l of ice-water, the biphasic mixture is stirred for 30 minutes and extracted with ether. The combined ether extracts are washed with water, dried and filtered and the solvent evaporated off leaving a brown oil which solidifies upon cooling. The solid is sublimed at 75° C/0.05 mm Hg to yield white crystals, mp 99°-101° C, of 4H,10H-pyrrolo[2,1-c][1,4]benzoxazepine.

Analysis:
Calculated for $C_{12}H_{11}NO$: 77.81%C; 5.99%H; 7.56%N.
Found: 77.7%C; 6.02%H; 7.5%N.

EXAMPLE 2

To 11 g of cold dimethylformamide is added dropwise with cooling 23 g of phosphorous oxychloride. This reagent is stirred at ambient temperature for 15 minutes and dissolved in 30 ml of 1,2-dichloroethane and the mixture cooled. To the cooled mixture is added dropwise 22 g of 4H,10H-pyrrolo[2,1-c][1,4]benzoxazepine in 40 ml of 1,2-dichloroethane. After total addition the reaction mixture is stirred at reflux for 3 hours and permitted to cool. To the reaction mixture is added a solution of 117 g of sodium acetate-trihydrate in 200 ml of water and the biphasic mixture is stirred at 85° C for 30 minutes. After the mixture is permitted to cool it is extracted with ether. The combined ether extracts are washed successively with a saturated sodium carbonate solution and water, dried and filtered and the solvent evaporated leaving a brown solid. The solid is recrystallized twice from ether to give the product, mp 126°-129° C, of 4H,10H-pyrrolo[2,1-c][1,4]benzoxazepine-1-carboxaldehyde.

Analysis:
Calculated for $C_{13}H_{11}NO_2$: 73.23%C; 5.20%H; 6.5%N.
Found: 73.32%C; 5.28%H; 6.54%N.

EXAMPLE 3

A Grinard reagent is prepared by the addition of a solution of 12.2 g in dimethylaminopropyl chloride in 50 ml of ether to give 2.4 g of magnesium turnings. To the Grignard reagent medium is added a solution of 7.0 g of 4H,10H-pyrrolo[2,1-c][1,4]benzoxazepine-1-carboxaldehyde, Example 2, and the reaction mixture is refluxed for 4 hours. The mixture is permitted to cool and poured into a 1 l of an ice cold ammonium chloride solution and the biphasic mixture is stirred for 30 minutes and extracted with chloroform. The combined chloroform extracts are washed with water, dried and filtered and the solvent removed leaving a yellow oil which solidifies upon trituration with petroleum ether. The solid is separated by filtration and the supernatant liquid is evaporated to dryness leaving an off-white solid. The solid is recrystallized from an ether-methanol mixture to give the product, mp 124°–125° C, of 4-dimethylamino-1-(4H,10H-pyrrolo[2,1-c][1,4]benzoxazepine-1-yl)-1-butanol.
Analysis:
Calculated for $C_{18}H_{24}N_2O_2$: 71.9%C; 8.05%H; 9.33%N.
Found: 71.88%C; 8.18%H; 9.21%N.

EXAMPLE 4

To a solution of 7.0 g of 4H,10H-pyrrolo[2,1-c][1,4]-benzoxazepine-1-carboxaldehyde, Example 2, and 8.6 g of 4,4-bis(4-fluorophenyl)butylamine in 50 ml of benzene is added 500 ml of cyclohexane and 25 g of a 3 A molecular seives and the reaction mixture is stirred at reflux for 4 days. The mixture is permitted to cool and filtered and the solvent evaporated off leaving a yellow oil. The oil is dissolved in ether and converted to a hydrochloride salt which is recrystallized from ethyl acetate to give the product, mp 120° c, dec., 1-[4,4-bis(4-fluorophenyl)-butyliminomethyl]4H,10H-pyrrolo[2,1-c][1,4]benzoxazepine-hydrochloride.
Analysis:
Calculated for $C_{29}H_{26}F_2N_2O \cdot HCl$: 70.65%C; 5.52%H; 5.68%N.
Found: 70.94%C; 4.78%H; 5.89%N.

EXAMPLE 5–7

By substituting the primary amines listed in Table II below for 4,4-bis-(4-fluororphenyl)butylamine in the treatment of 4H,10H-pyrrolo[2,1-c][1,4]benzoxazepine-1-carboxaldehyde (Example 2) according to the procedure of Example 4, the corresponding imino compounds of the invention are formed:

N,N-diethylaminoethyl-(Example 5), phenethyl-(Example 6) and methyl-(Example 7) imino compounds of the invention are formed.

EXAMPLE 8

A mixture of 8.0 g of 1-[4,4-bis-(4-fluorophenyl)-butyliminomethyl]- 4H,10H-pyrrolo[2,1-c][1,4]benzoxazepine, Example 4, and 1.52 g of sodium borohydride in 250 ml of ispropyl alcohol is refluxed for 20 hours and the solvent removed leaving a white solid. The solid is stirred with 500 ml of water and extracted into ether. The combined ether extracts are washed, dried and filtered and the ether removed leaving a yellow oil which is converted to a hydrochloride salt. The salt is recrystallized twice from ethyl acetate to give the product, mp 130° C, dec., of 1-[4,4-bis-(4-fluorophenyl)-butylaminomethyl]-4H,10H-pyrrolo[2,1-c][1,4]benzoxazepine hydrochloride.
Analysis:
Calculated for $C_{29}H_{28}F_2N_2O \cdot HCl$: 70.36%C; 5.91%H; 5.66%N.
Found: 70.20%C; 6.24%H; 5.71%N.

EXAMPLE 9 and 10

By analagous reduction of the imino compounds of Examples 6 and 7 and treatment as described in Example 8, the corresponding 1-phenethylaminomethyl-(Example 9) and 1-methylaminomethyl- (Example 10)-4H,10-H-pyrrolo-[2,1-c][1,4]benzoxazepine-hydrochlorides of the invention listed below in Table III are formed.

TABLE III

| | | | | | Analysis | | | | | |
|---|---|---|---|---|---|---|---|---|---|---|
| | | | | | Calc'd | | | Found | | |
| Ex. | Starting Material | Recryst'n Solvent | mp °C | Empirical Formula | %C | %H | %N | %C | %H | %N |
| 9 | 6 | i-Pr-OH—ether | 140, dec. | $C_{21}H_{22}N_2O \cdot HCl$ | 71.07 | 6.53 | 7.90 | 70.71 | 6.76 | 7.84 |
| 10 | 7 | ethyl acetate-MeOH | 145°, dec. | C H N O HCl | 63.51 | 6.47 | 10.58 | 63.66 | 6.90 | 10.73 |

EXAMPLE 11

To a cooled solution of 5.0 g of 1-methylaminomethyl-4H, 10H-pyrrolo[2,1-c][1,4]benzoxazepine, free base of Example 10, and 4.1 ml of triethylamine in 50 ml of chloroform is added dropwise a solution of 3.1 g of cyclopropylcarbonyl chloride in 25 ml of chloroform. After total addition the reaction mixture is stirred at ambient temperature for 30 hours, washed with water, dried and filtered and the chloroform removed leaving a yellow oil. The oil is dissolved in 50 ml of tetrahydrofuran and added to a refluxing solution of 1.90 g of lithium aluminum hydride in 150 ml of tetrahydrofuran. The mixture is stirred at 65° C for 20 hours, permitted to cool, quenched with 60 ml of saturated ammonium chloride solution, and filtered. The organic phase of the mixture is collected, diluted with ether, washed with water, dried and filtered and the solvent removed leaving a dark oil. The oil is converted to a hydrochloride salt which is recrystallized from an ethyl acetate-methanol mixture to give the product, mp 120° C, dec., of 1-[(N-cyclopropylmethyl-N-methyl)aminomethyl]-4H,10H-pyrrolo[2,1-c][1,4]benzoxazepine. hydrochloride.
Analysis:
Calculated for $C_{18}H_{22}N_2O \cdot HCl$: 67.80%C; 7.27%H; 8.79%N.
Found: 67.76%C; 7.79%H; 8.66%N.

EXAMPLE 12

To a cold solution of 8.0 g of 1-[(N-phenethyl)aminomethyl]-4H,10H-pyrrolo[2,1-c][1,4]benzoxazepine, free base of Example 9, and 3.0 g of triethylamine in 50 ml of chloroform is added dropwise a solution of

TABLE II

| | | | | | Analysis | | | | | |
|---|---|---|---|---|---|---|---|---|---|---|
| | Primary | Recryst'n | m.p. | Empirical | Calc'd | | | Found | | |
| Ex. | Amine | Solvent | °C | Formula | %C | %H | %N | %C | %H | %N |
| 5 | N,N-diethylaminoethylamine | ethyl acetate—MeOH | 110, dec. | $C_{19}H_{25}N_3O \cdot HCl \cdot 2H_2O$ | 59.44 | 7.88 | 10.95 | 59.97 | 7.62 | 11.20 |
| 6 | phenethylamine | pet ether | 76–79 | $C_{21}H_{20}N_2O$ | 79.72 | 6.37 | 8.85 | 79.69 | 6.24 | 8.99 |
| 7 | methylamine | pet ether | 114–117 | $C_{14}H_{14}N_2O$ | 74.31 | 6.24 | 12.38 | 74.35 | 6.36 | 12.69 |

3.3 g of ethyl chloroformate in 25 ml of chloroform. After total addition the reaction mixture is stirred at ambient temperature for 20 hours, washed with water, dried and filtered and the chloroform removed leaving a yellow oil. The oil is dissolved in 50 ml of tetrahydrofuran and then added dropwise to a refluxing mixture of 1.9 g of lithium aluminum hydride in 150 ml of tetrahydrofuran. Refluxing is continued for 20 hours and then the reaction mixture is cooled, quenched with 60 ml of a saturated ammonium chloride solution, diluted with 200 ml of ether and filtered. The organic phase of the mixture is collected, washed with water dried and filtered and the solvent removed leaving a clear oil. The oil is converted to a hydrochloride salt which is recrystallized from an isopropyl alcohol-ether mixture to give the product, mp 130° C, dec., of 1-(N-methyl-N-phenethylaminomethyl)-4H,10H-pyrrolo[2,1-c][1,4]benzoxazepine hydrochloride.

Analysis:

Calculated for $C_{22}H_{24}N_2O \cdot HCl$: 71.62%C; 6.83%H; 7.60%N.

Found: 72.00%C; 7.33%H; 7.71%N.

EXAMPLE 13

The treatment of 1-methylaminomethyl-4H, 10H-pyrrolo[2,1-c]- [1,4]benzoxazepine, free base of Example 10, by a procedure analogous to the procedure described in Example 12 produces a hydrochloride salt which is recrystallized twice from an acetone-methanol mixture to give the product, mp 153° C., dec., of 1-dimethylaminomethyl-4H,10H-pyrrolo[2,1-c][1,4]benzoxazepine hydrochloride.

Analysis:

Calculated for $C_{15}H_{18}N_2O \cdot HCl$: 64.62%C; 6.87%H; 10.05%N.

Found: 65.20%C; 7.48%H; 9.76%N.

EXAMPLE 14 a. The treatment of 1-(4-chloro-2-fluorobenzyl)pyrrole according to the procedure described in Example 1b produces 1-(4-chloro-2-fluorobenzyl)pyrrole-2-carboxaldehyde.

b. The reduction and treatment of 1-(4-chloro-2-fluorobenzyl)pyrrole-2-carboxaldehyde by the procedure described in Example 1c produces [1-(4-chloro-2-fluorobenzyl)-2-pyrryl]methanol.

c. The condensation and treatment of [1-(4-chloro-2-fluorobenzyl)-2-pyrryl]methanol by the procedure described in Example 1d produces 7-chloro-4H,10H-pyrrolo[2,1-c][1,4]benzoxazepine.

EXAMPLE 15 a. The treatment of (2-fluorophenethyl)pyrrole according to the procedure described in Example 1b produces 1-(2-fluorophenethyl)pyrrole-2-carboxaldehyde.

b. The reduction and treatment of 1-(2-fluorophenethyl)pyrrole-2-carboxaldehyde according to the procedure described in Example 1e produces [1-(2-fluorophenethyl)-2-pyrryl]methanol.

c. The condensation and treatment of [1-(2-fluorophenethyl)-2-pyrryl]methanol according to the procedure described in Example 1d produces 10,11-dihydro-4H-pyrrolo[2,1-c][1,4]benzoxazocine.

We claim:
1. A compound of the formula

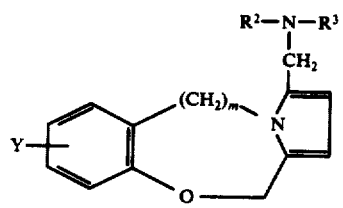

wherein Y is hydrogen, halogen, lower alkoxy, lower alkyl, trifluoromethyl, nitro or amino; $R^2$ is alkyl, phenylloweralkyl, alkylaminoalkyl, dialkylaminoalkyl or diphenylloweralkyl of the formula

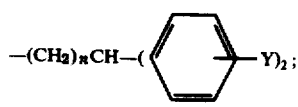

and $R^3$ is hydrogen, alkyl, cycloalkylloweralkyl or phenylloweralkyl; $m$ the integer 1 or 2; or a physiologically tolerable acid addition salt thereof.

2. A compound as defined in claim 1 wherein $m$ is the integer 1.

3. A compound as defined in claim 1 wherein Y is hydrogen halogen, nitro or methyl; and $R^2$ is alkyl, phenylloweralkyl, alkylaminoalkyl, dialkylaminoalkyl, $(CH_2)_n CH-(C_6H_5)_2$ or

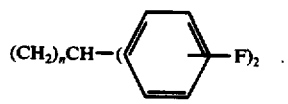

4. A compound as defined in claim 3 wherein Y is hydrogen, $R^2$ is methyl, phenethyl, N,N-diethylaminoethyl or

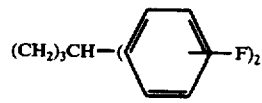

and $R^3$ is hydrogen, methyl or cyclopropylmethyl.

5. A compound as defined in claim 1 wherein $m$ is the integer 2.

6. The compound defined in claim 1 which is 1-[(N-phenethyl)aminoethyl - 4H,10H-pyrrolo[2,1-c][1,4]benzoxazepine.

7. The compound defined in claim 1 which is 1-[4,4-bis-(4-fluorophenyl) butylaminomethyl]-4H,10H-pyrrolo[2,1-c][1,4]benzoxazepine.

8. The compound defined in claim 1 which is 1-methylaminomethyl- 4H,10H-pyrrolo[2,1-c][1,4]benzoxazepine.

9. The compound defined in claim 1 which is 1-dimethylaminomethyl-4H,10H-pyrrolo[2,1c][1,4]benzoxazepine.

* * * * *